(12) United States Patent
Abdullah et al.

(10) Patent No.: US 11,859,164 B2
(45) Date of Patent: Jan. 2, 2024

(54) STACKED MEMBRANE BIOREACTOR

(71) Applicant: Battelle Memorial Institute, Columbus, OH (US)

(72) Inventors: Zia Abdullah, Bexley, OH (US); Michael L. Dickens, Westerville, OH (US); Micah Paul McCreery, Baltimore, OH (US); Randy L. Jones, Delaware, OH (US); Elvin Ray Beach, III, Columbus, OH (US); Jon-David S. Sears, Columbus, OH (US); Erin Suzanne Schultz, Dublin, OH (US); Stephanie Ann Smith, Columbus, OH (US); Paul E. George, II, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 262 days.

(21) Appl. No.: 17/230,387

(22) Filed: Apr. 14, 2021

(65) Prior Publication Data

US 2021/0238529 A1    Aug. 5, 2021

Related U.S. Application Data

(62) Division of application No. 15/484,084, filed on Apr. 10, 2017, now Pat. No. 11,008,541, which is a (Continued)

(51) Int. Cl.
*C12M 3/00*    (2006.01)
*C12M 1/00*    (2006.01)
(Continued)

(52) U.S. Cl.
CPC ............ *C12M 29/04* (2013.01); *C12M 23/24* (2013.01); *C12M 23/34* (2013.01); *C12M 23/40* (2013.01);
(Continued)

(58) Field of Classification Search
CPC ....... C12M 23/34; C12M 23/40; C12M 23/24
See application file for complete search history.

(56) References Cited

U.S. PATENT DOCUMENTS

| 3,711,259 A | 1/1973 | Gurney |
| 4,661,458 A | 4/1987 | Berry et al. |

(Continued)

FOREIGN PATENT DOCUMENTS

| CN | 101451103 A | 6/2009 |
| EP | 0363262 A1 | 4/1990 |

(Continued)

OTHER PUBLICATIONS

International Search Report and Written Opinion in International Application No. PCT/US2012/070686, dated Jul. 15, 2013 (10 pages).

*Primary Examiner* — Nathan A Bowers
(74) *Attorney, Agent, or Firm* — BENESCH, FRIEDLANDER, COPLAN & ARONOFF LLP (57) ABSTRACT

Scalable biomaterial-based bioreactors are described. In one embodiment, the bioreactor may comprise perforated plates stacked such that the assembled bioreactor has the necessary manifolds and chambers to transport gas and liquids to a biomaterial contained within the bioreactor, and to remove the reaction products. In another embodiment, single use bioreactors are described. Methods of operating the bioreactors are also described.

5 Claims, 6 Drawing Sheets

Related U.S. Application Data division of application No. 14/367,231, filed as application No. PCT/US2012/070686 on Dec. 19, 2012, now abandoned.

(60) Provisional application No. 61/577,225, filed on Dec. 19, 2011.

(51) Int. Cl.
*C12M 1/04* (2006.01)
*C12M 1/34* (2006.01)
*C12P 3/00* (2006.01)

(52) U.S. Cl.
CPC ............ *C12M 23/44* (2013.01); *C12M 41/00* (2013.01); *C12P 3/00* (2013.01)

(56) References Cited

U.S. PATENT DOCUMENTS

| | | | |
|---|---|---|---|
| 4,937,196 A | 6/1990 | Wrasidlo et al. | |
| 4,940,547 A | 7/1990 | Cho et al. | |
| 4,976,931 A | 12/1990 | Stoermer, III | |
| 5,686,304 A | 11/1997 | Codner | |
| 6,228,607 B1 | 5/2001 | Kersten et al. | |
| 6,844,187 B1 | 1/2005 | Weschsler et al. | |
| 7,560,274 B1 | 7/2009 | Fuller et al. | |
| 2004/0045890 A1 | 3/2004 | Herczeg | |
| 2006/0014274 A1 | 1/2006 | Klaus | |
| 2007/0042490 A1 | 2/2007 | Welter et al. | |
| 2011/0143334 A1 | 6/2011 | Roscoe | |
| 2011/0226686 A1 | 9/2011 | Maurer | |
| 2013/0149755 A1* | 6/2013 | Reed .................... | C12P 7/6463 204/278 |
| 2014/0323694 A1 | 10/2014 | Von Keitz et al. | |

FOREIGN PATENT DOCUMENTS

| | | |
|---|---|---|
| WO | 96/26264 A | 8/1996 |
| WO | 2011139804 A2 | 11/2011 |

* cited by examiner

STACKED MEMBRANE BIOREACTOR

CROSS-REFERENCE TO RELATED APPLICATIONS

This application is a divisional of U.S. patent application Ser. No. 15/484,084 filed Apr. 10, 2017, which is a divisional of U.S. patent application Ser. No. 14/367,231 filed Jun. 19, 2014, which is a National Stage of PCT/US2012/070686 filed Dec. 19, 2012, which claims priority from U.S. Provisional Patent Application No. 61/577,225 filed Dec. 19, 2011. The entire contents of each of these applications are incorporated by reference herein.

STATEMENT REGARDING FEDERALLY SPONSORED RESEARCH OR DEVELOPMENT

This invention was made with government support under DE-AR0000095 awarded by The Advanced Research Projects Agency-Energy (ARPA-E) to The Ohio State University. The government has certain rights in the invention.

BACKGROUND $CO_2$ is produced in many commercial processes. Excessive emission of $CO_2$ is damaging to the atmosphere. Thus, it would be desirable to capture and use at least some of the $CO_2$ produced in commercial processes, if only to reduce $CO_2$ emissions into the atmosphere.

One potential use for the $CO_2$ produced in commercial processes is in the production of short and medium-length alkanols for, e.g., fuel. For example, ethanol and butanol may be used as fuel in an internal combustion engine. Butanols longer hydrocarbon chain causes it to be fairly non-polar and, thus, butanol is more similar to gasoline than ethanol is. In fact, butanol has been demonstrated to work in vehicles designed for use with gasoline without modification.

Toward this end, bioreactors are being investigated to produce products, including fuels, from $CO_2$, $H_2$, and $O_2$. Two basic methods appear promising: One involves biomaterials that use sunlight to convert $CO_2$, such as phototrophic bacteria or algae; and another involves biomaterials that can use $H_2$ directly and do not require sunlight, such as some types of bacteria.

However, there are a number of practical problems in developing bioreactors. One problem relates to the biological aspect of the bioreactors, e.g., what biomaterial to use (bacteria or algae, and what type), and how and whether to modify the biomaterial. Another problem involves the design of the bioreactor. For example, supply of $H_2$ and $O_2$ to the biomaterial involves significant safety issues because of the potentially explosive nature of the mixture of the gases.

What is needed is a safe, scalable bioreactor that efficiently converts $CO_2$, $H_2$, and $O_2$, and perhaps other hydrocarbons or other carbon/hydrogen-rich compounds (in gas or liquid form) into useful products, including, but not limited to, fuels.

SUMMARY

In one embodiment, a bioreactor is provided, the bioreactor comprising; biomaterial reactor chamber; a gas reactor chamber in fluid communication with a first side of the biomaterial reactor chamber; a medium reactor chamber in fluid communication with a second side of the biomaterial reactor chamber; a gas inlet and a gas outlet in fluid communication with the gas reactor chamber; and a medium inlet and a medium outlet in fluid communication with the medium reactor chamber.

In another embodiment, a bioreactor is provided, the bioreactor comprising: manifold plate having a gas inlet, a gas outlet, a medium inlet, and a medium outlet; a gas delivery plate having a gas reactor chamber, a gas inlet manifold in fluid communication with the gas reactor chamber and the gas inlet, a gas outlet manifold in fluid communication with the gas reactor chamber and the gas outlet, a medium inlet manifold in fluid communication with the medium inlet, and a medium outlet manifold in fluid communication with the medium outlet; a biomaterial plate having a biomaterial reactor chamber, a gas inlet manifold in fluid communication with the gas delivery plate gas inlet manifold, a gas outlet manifold in fluid communication with the gas delivery plate gas outlet manifold, a medium inlet manifold in fluid communication with the gas delivery plate medium inlet manifold, and a medium outlet manifold in fluid communication with the gas delivery plate medium outlet manifold; a medium delivery plate having a medium reactor chamber; a gas inlet manifold in fluid communication with the biomaterial plate gas inlet manifold, a gas outlet manifold in fluid communication with the biomaterial plate gas outlet manifold, a medium inlet manifold in fluid communication with the medium reactor chamber and the biomaterial plate medium inlet manifold, and a medium outlet manifold in fluid communication with the medium reactor chamber and the biomaterial plate medium outlet manifold; and an end plate.

In another embodiment, a bioreactor is provided, the bioreactor comprising: a first outer shell; a hydrophilic membrane; a biomaterial; a hydrophobic membrane; optionally, a flame arrestor; and a second outer shell.

In another embodiment, a method for making a bio-based product is provided, the method comprising: introducing $H_2$ gas into a bioreactor on a first side of a biomaterial reactor chamber containing biomaterial; introducing medium containing $O_2$ into the bioreactor on a second side of the biomaterial reactor chamber; introducing $CO_2$ into the bioreactor on the first side, the second side, or both, wherein the biomaterial produces the bio-based product from the $H_2$, the $CO_2$, and the $O_2$; and outletting and/or removing the bio-based product from the bioreactor.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale, and that the various shapes (e.g., rectangular, square) depicted in the figures are presented for purposes of illustration only, and should not be considered in any way as limiting.

DETAILED DESCRIPTION

The invention involves novel, safe, scalable, biomaterial-based bioreactors and method of using the same. In one embodiment, the bioreactor is made using perforated plates stacked such that the assembled bioreactor has the necessary manifolds and chambers to transport gas and liquids to the biomaterial and to remove the reaction products.

In one embodiment, the bioreactor may be used to contact gases and liquid medium with a reactor chamber containing, biomaterial. As used herein, the term "biomaterial" is intended, at a minimum, to cover all types of biomaterial that can be used to convert $CO_2$ to bio-based products, including but not limited to, bacteria and algae. The term "biomaterial" may also include biomaterial that does not use and/or require $CO_2$. In one embodiment, the biomaterial comprises a living organism capable of using hydrogen gas as a source of energy. In one embodiment, the biomaterial comprises bacteria capable of using hydrogen gas as a source of energy. In one embodiment, the biomaterial, is an autotroph. In one embodiment, the biomaterial comprises *Ralstonia eutropha*, e.g., H16 or *Cupriavidus*. In another embodiment, the reactor may be used to grow anaerobic organisms (using oxygen nonpermeable membranes about the biomaterial) and aerobic organisms that use alternative carbon sources.

In one embodiment, the biomaterial reactor chamber may contain a natural or artificial biofilm grown on a membrane or other fibrous support structure, or the biomaterial can be sandwiched in a chamber cavity between two membranes. On one side of the biomaterial reactor chamber containing the biomaterial, a gas, such as hydrogen, may be introduced. On the opposite side of the chamber, a liquid medium, providing nutrients, oxygen, and carbon dioxide for the biomaterial may be circulated. Thus, in at least one embodiment, when a first element is said to be "in fluid communication with" a second element (e.g., a gas reactor chamber "in fluid communication with" a first side of the biomaterial reactor chamber; or a medium reactor chamber "in fluid communication with a second side of the biomaterial reactor chamber") in fact, the two elements may be in fluid communication through the membrane(s).

The liquid medium may comprise any suitable liquid medium that may supply nutrients and oxygen, and, in some embodiments, carbon dioxide, such as are well known in the art. For example, the liquid medium may comprise Repaske's medium or a modified version thereof. The biomaterial converts the carbon dioxide to bio-based products or another product(s), which can be outletted or otherwise removed on either the gas, side or the liquid medium side.

In various embodiments, the bioreactor may be used to make bio-based products, including, but not limited to, lubricants and greases, lubricant additives, biofuels bio-based chemicals, oil remediation dispersants and sorbents, health supplements, nutraceutical, cosmeceufical, and pharmaceutical product ingredients, horticultural and aquacultural feed or supplements, and intermediates to the foregoing. As used herein, the term "biofuels" broadly refers to bio-based products suitable for use as a fuel or a combustion source, including fuels suitable for transportation and power generation. Biofuels include, but are not limited to, biogasoline, biodiesel, jet fuels, ethanol, methanol, butanol, and the like. Bio-based materials and chemicals include, but are not limited to: Polyhydmxyalkanoates, lactic acid, acetic acid, succinic acid, malic acid, 1-butanol, isobutanol, 2-butanol, other alcohols, amino acids, 1,3-propanediol, ethylene, glycerine, β-lactam antibiotics, cephalosporin, alkanes, terpenes, and the like.

In one embodiment, the bioreactor may be made up of a stack of plates. Each plate may be stamped with a perforation pattern such that when the plates are stacked together, a bioreactor is created, with gas and medium reactor chambers on each side of a biomaterial reactor chamber containing the biomaterial. Gas may be supplied on one side of the biomaterial reactor chamber through gas manifolds, and medium may be supplied on the other side of the biomaterial reactor chamber through medium manifolds.

In some embodiments, costs for preparation of the bioreactor may be minimized because the plates can be mass produced using a stamping process. In addition, in some embodiments, reactor capacity may be readily scalable by increasing the number of plates in the stack and/or the dimensions of the membranes. The reactor may also provide increased safety, as the small size of each individual cell will limit the magnitude of potentially destructive energy release. If desirable or appropriate, flame arrestors may be added in the gas manifolds, as well as between the plates, to prevent flame propagation if hydrogen and oxygen were to react explosively.

In some, embodiments, the reactor may be configured so that different reactions take place in adjacent cells. In one embodiment, the stacked reactors may be configured so that products produced in one reactor become feedstocks for another reactor, and so forth, like a daisy chain to the final product. For example:

Stack Reactor 1=Product 1 (feedstock for Reactor 2)→Stack Reactor 2=Product 2 (feedstock for Reactor 3)→→→final product.

For example, hydrogen can be produced by one type of biomaterial in one cell, and this hydrogen can be transported to an adjacent cell, where it can be used as a feedstock to produce a secondary product. In another example, other intermediates (e.g., metabolites, peptides, building blocks) may be prepared and/or supplied for more complex products. Indeed, using such a design may provide for practically limitless bioconversions (e.g., chiral specific conversions of pharmaceuticals and their precursors, as well as oxygenation and/or dehydrogenation and/or methylation and/or acetylation, of numerous compounds). The possibilities are vast and, in view of disclosure of the present application, achievable.

In one embodiment, $CO_2$ may be supplied in the form of $CO_2$ emitted from a commercial process. In one embodiment, $CO_2$, $H_2$, and hydrocarbon or hydrocarbon-like (hydrogen and carbon-rich) gas may be supplied in the form of a product from pyrolysis of a biomass.

Figures 1A, 1B, 1C, 1D, 1E:
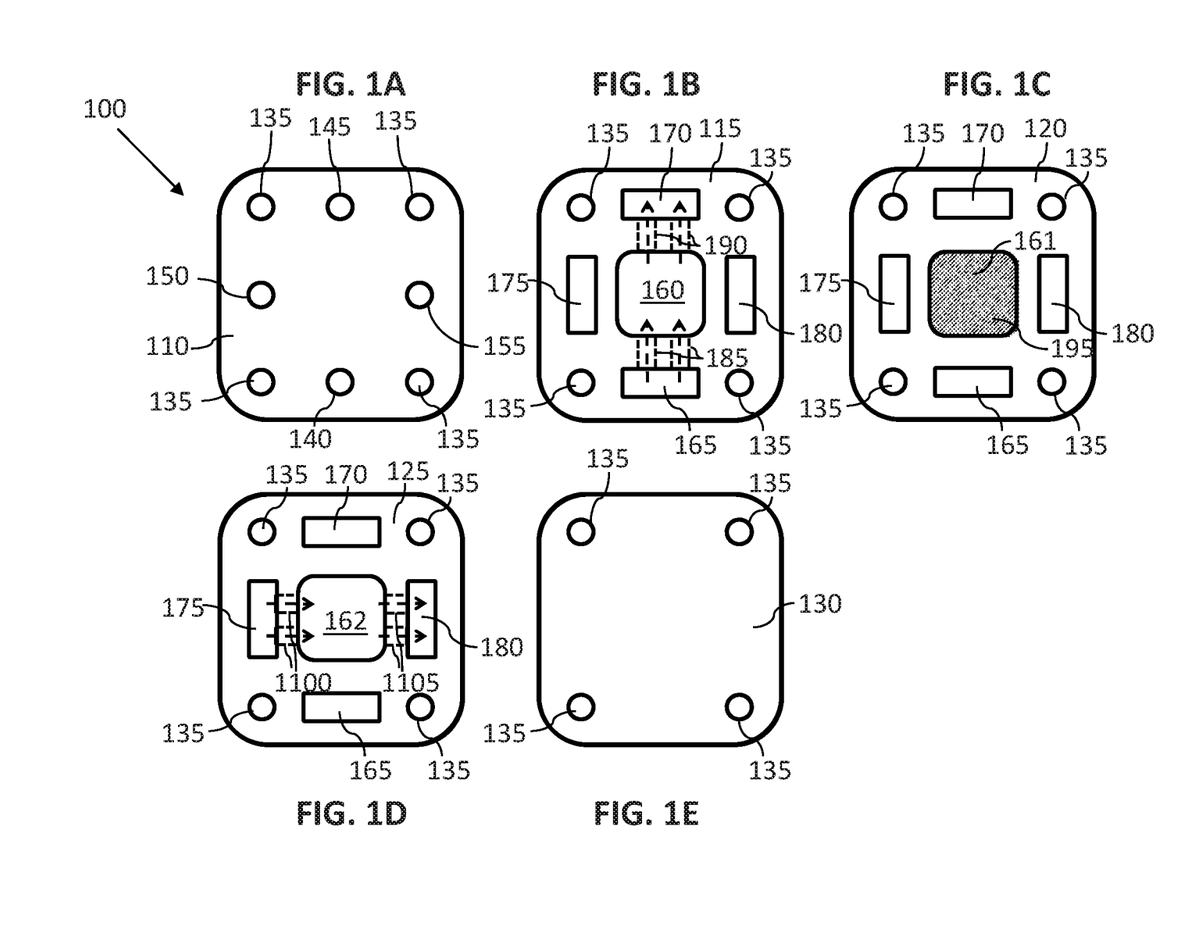
FIGS. 1A-E are illustrations of different plates used in one embodiment of a stacked bioreactor 100.
Figure 2:
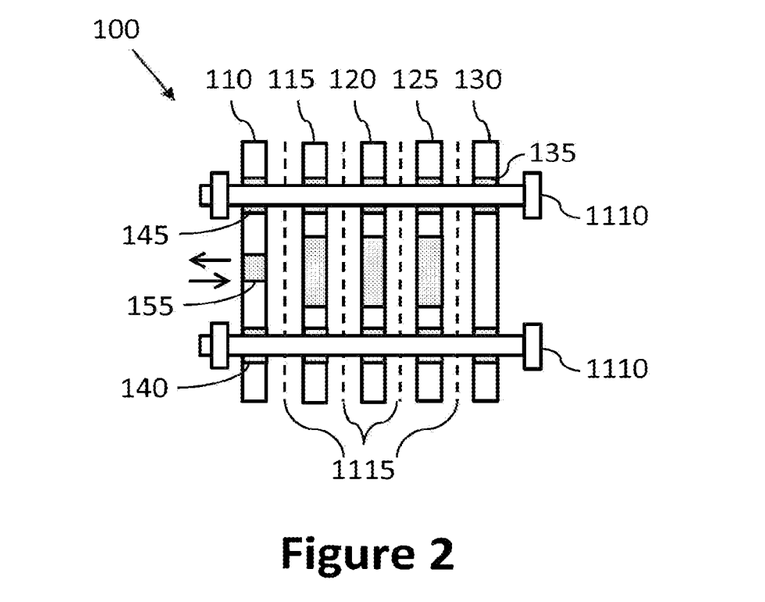
FIG. 2 is an illustration of one embodiment of an assembled stacked bioreactor 100.
Figure 3:
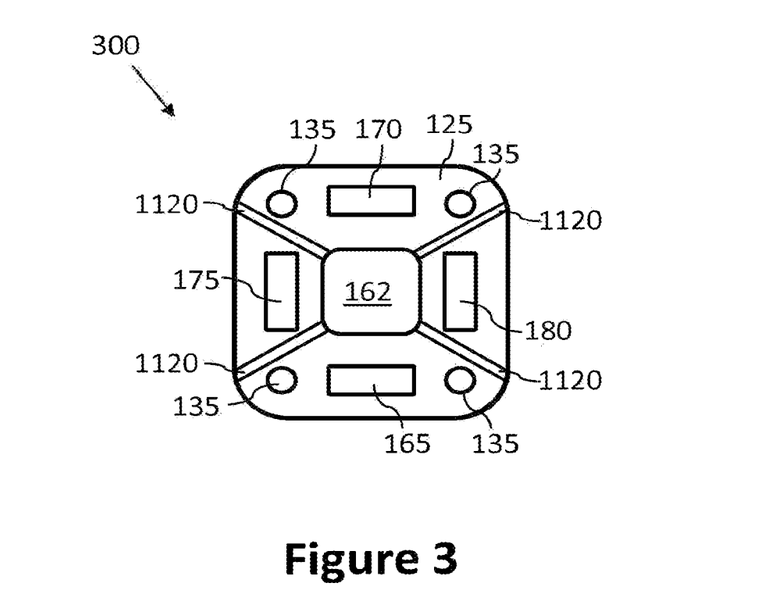
FIG. 3 is an illustration of an alternate embodiment of a medium delivery plate 300.
Figure 4A:
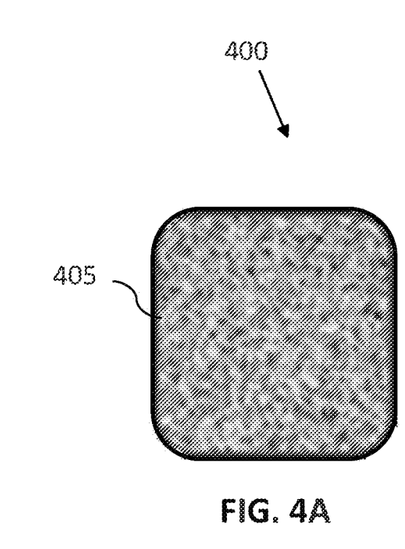
FIGS. 4A-E are illustrations of the different structures used in one embodiment of a membrane assembly 400 for a stacked bioreactor.
Figure 4B:
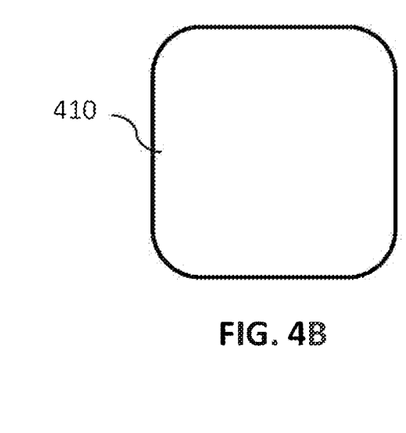
Figure 4C:
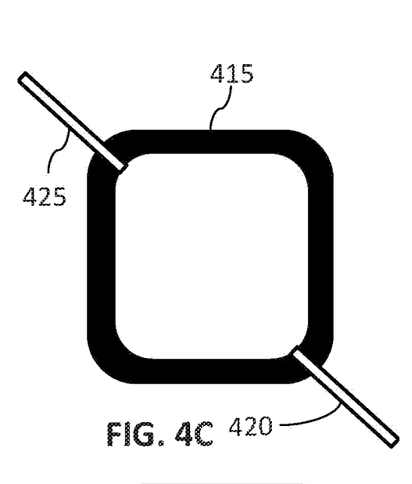
Figure 4D:
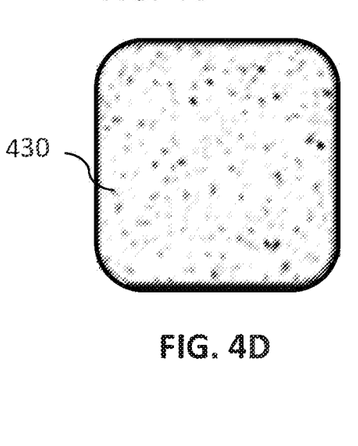
Figure 4E:
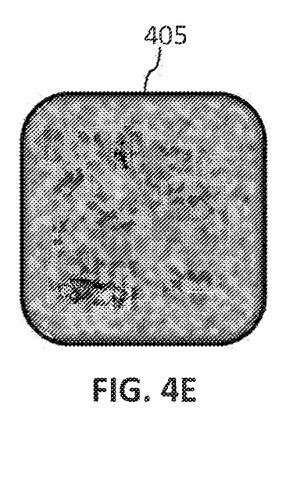
Figure 5:
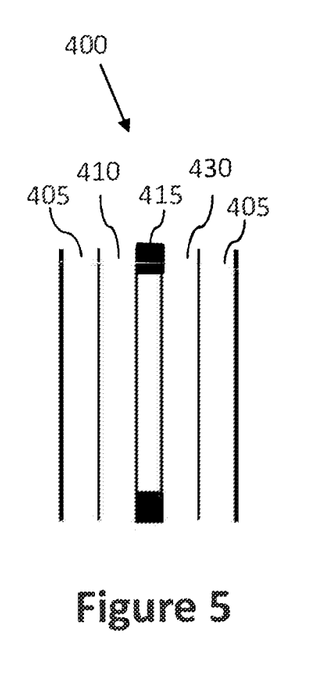
FIG. 5 is an illustration of one embodiment of membrane assembly 400 for use in a stacked bioreactor.
Figure 6:
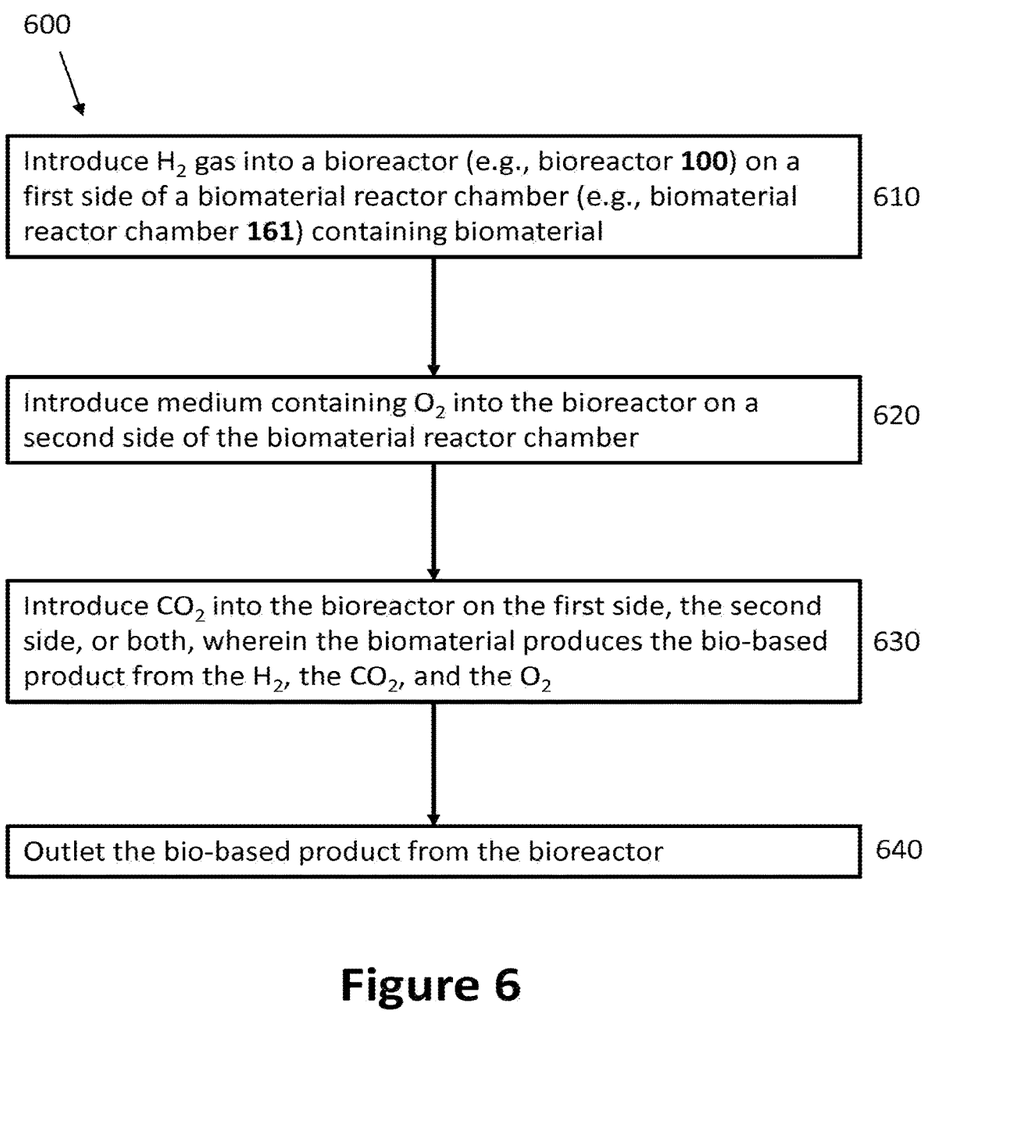
FIG. 6 is a flowchart depicting an example method 600 for making a bio-based product.
Figure 7:
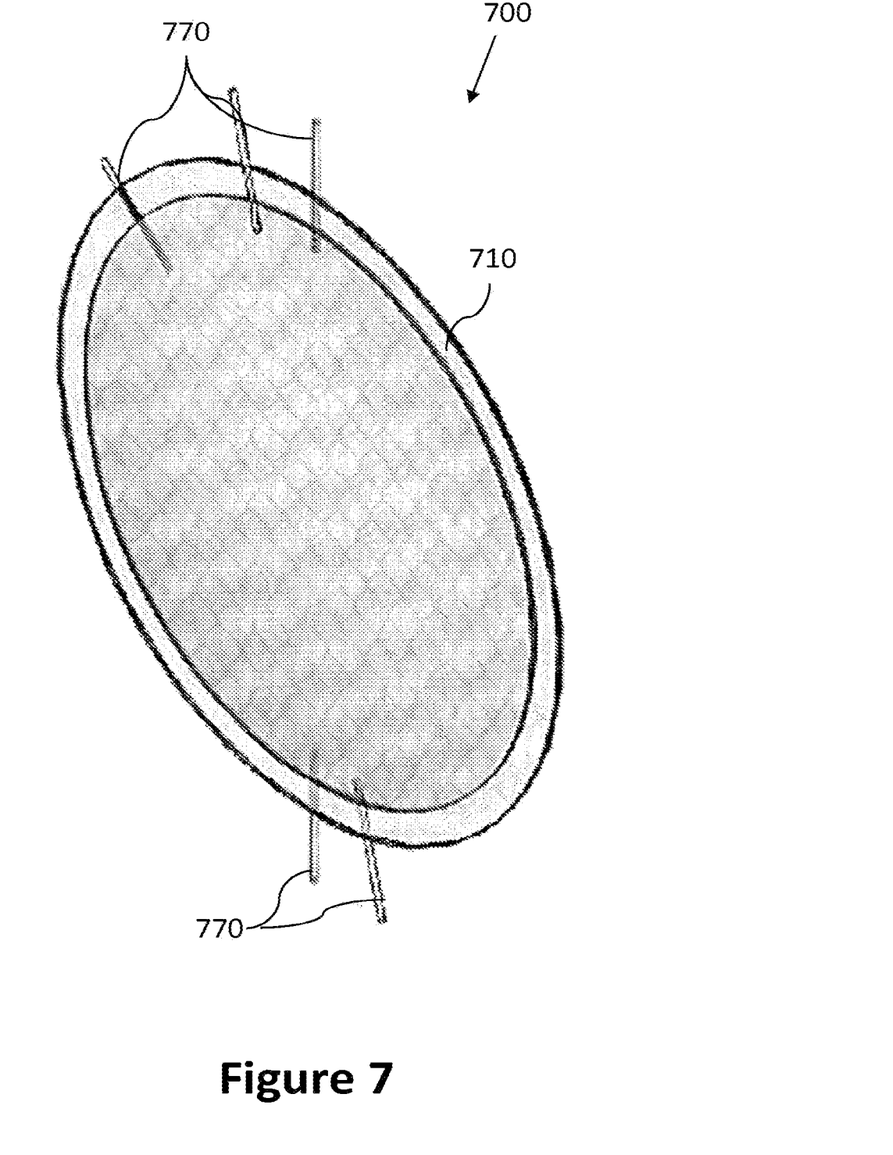
FIG. 7 is an illustration of one embodiment of a membrane assembly 700 for use as a single use gas exchange membrane bioreactor.
Figure 8:
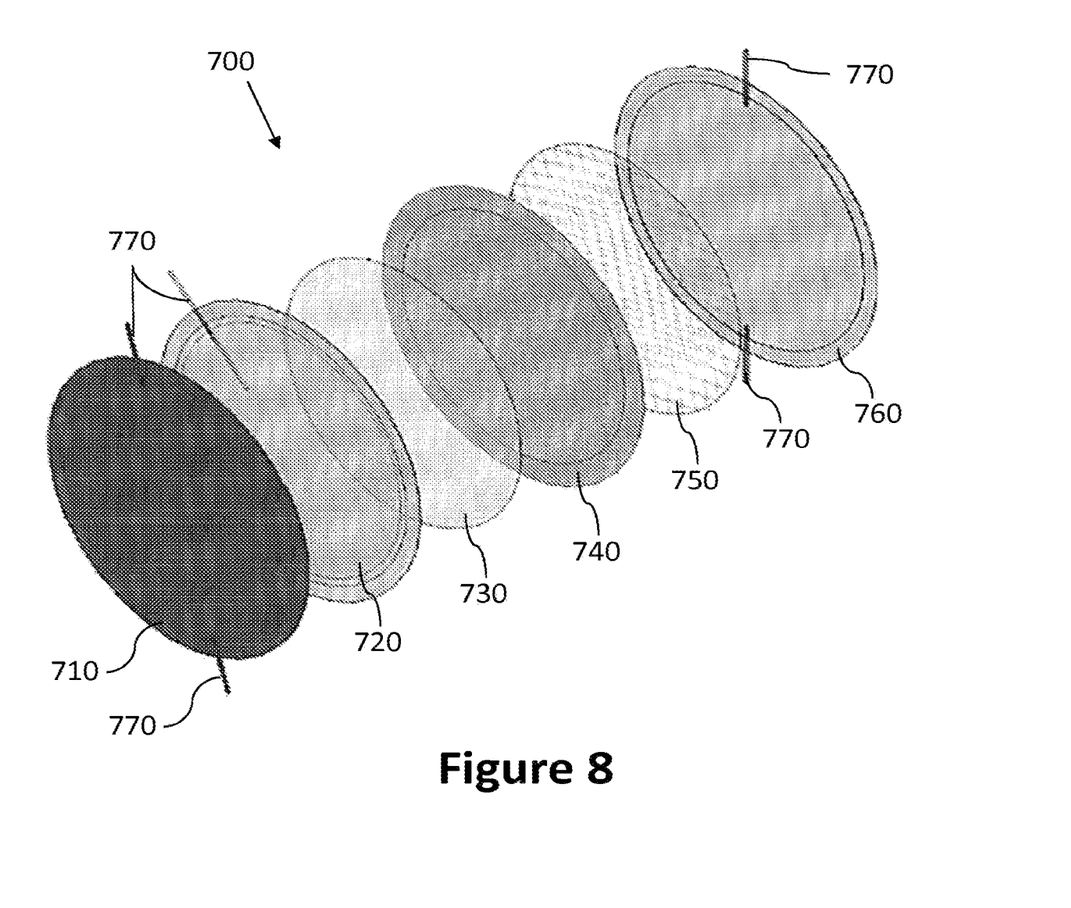
FIG. 8 is an exploded view of one embodiment of membrane assembly 700 for use as a single use gas exchange membrane bioreactor.

FIGS. 1-2 illustrate one embodiment of a bioreactor 100. More specifically, FIGS. 1A-E illustrate a series of plates that can be used to form one embodiment of bioreactor 100. FIG. 1A illustrates manifold plate 110. FIG. 1B shows a gas delivery plate 115. FIG. 1C shows a biomaterial plate 120. FIG. 1D shows a medium delivery plate 125. And FIG. 1E shows an end plate 130.

The plates can be made of any suitable material, such as metal, plastic, ceramic, acrylic, polycarbonate, polypropylene, Delrin® manufactured by Dupont, polyetheretherketone, polyvinyl chloride (PVC), stainless steel, and the like. The plates can be any suitable shape, such as square, rectangular, circular, and the like.

The bioreactor may be secured together in any suitable manner, as would be understood by those of skill in the art. For example, bolts, screws, or clamps may be used. In some embodiments, adjacent plates could have interlocking parts to secure the adjacent plates together. The interlocking parts may be releasable or permanent. For instance, permanent interlocks may be used if the bioreactor was to be disposable and not intended to be disassembled. In one embodiment, each of the plates has bolt holes 135 on the corners for bolting the plates together to assemble the bioreactor.

As shown, manifold plate 110 has a gas inlet 140 and a gas outlet 145 on two opposing sides, and a medium inlet 150 and medium outlet 155 on the other two opposing sides of manifold plate 110.

As shown, gas delivery plate 115 has a gas reactor chamber 160 in the middle, biomaterial plate 120 has a biomaterial reactor chamber 161 in the middle, and medium delivery plate 125 has a medium reactor chamber 162 in the middle. Gas delivery plate 115 has a gas inlet manifold 165 and a gas outlet manifold 170 on opposite sides of the plate outside of gas reactor chamber 160, and a medium inlet manifold 175 and a medium outlet manifold 180 outside of gas reactor chamber 160 on the other two opposing sides. Biomaterial plate 120 has a gas inlet manifold 165 and a gas outlet manifold 170 on opposite sides of the plate outside of biomaterial reactor chamber 161, and a medium inlet manifold 175 and a medium outlet manifold 180 outside of biomaterial reactor chamber 161 on the other two opposing sides. Medium delivery plate 125 has a gas inlet manifold 165 and a gas: outlet manifold 170 on opposite sides of the plate outside of medium reactor chamber 162, and a medium inlet manifold 175 and a medium outlet manifold 180 outside of medium reactor chamber 162 on the other two opposing sides.

As shown, gas delivery plate 115 has gas inlet channels 185 between gas inlet manifold 165 and gas reactor chamber 160, and gas outlet channels 190 between gas reactor chamber 160 and gas outlet manifold 170.

Biomaterial plate 120 may have a membrane 195 in biomaterial reactor chamber 161. In one embodiment, membrane 195 may contain an artificial or natural biofilm which is used to immobilize biomaterial. Membrane 195 may be fabricated using composite materials and may serve to provide one or more of the following attributes: (a) structural support or scaffolding to the biofilm; (b) a seal between the gas and the medium phases; and (c) pathways for the gases, nutrients, and products to and from the biomaterial immobilized in the biofilm. Alternatively, biomaterial reactor chamber 161 may contain free-floating biomaterial.

As shown, medium delivery plate 125 has medium inlet channels 1100 between medium inlet manifold 175 and medium reactor chamber 162, and medium outlet channels 1105 between medium reactor chamber 162 and medium outlet manifold 180.

In one embodiment, end plate 130 may be solid except for bolt holes 135.

In one embodiment, plates 110, 115, 120, 125, and 130 are bolted together by placing bolts 1110 in bolt holes 135 in the corners of the plates, as shown in FIG. 2. There may additionally be gaskets 1115 between plates 110, 115, 120, 125, and 130 to seal bioreactor 100.

In one embodiment, $H_2$ gas may enter bioreactor 100 through gas inlet 140 in manifold plate 110, and may flow through gas inlet channels 185 in gas delivery plate 115 into gas reactor chamber 160, where the gas is available for use by the biomaterial on membrane 195 in biomaterial reactor chamber 161. The gas flows out, through gas outlet channels 190 to gas outlet manifold 170, and exits bioreactor 100 through gas outlet 145 in manifold plate 110.

In one embodiment, medium may enter bioreactor 100 though medium inlet 150 in manifold plate 110. In one embodiment, $O_2$ and $CO_2$ are mixed in the medium. Medium flows through medium inlet manifold 175 in gas delivery plate 115, biomaterial plate 120, and medium delivery plate 125. The medium flows through medium inlet channels 1100 to medium reactor chamber 162 in medium delivery plate 125, where the medium is available for use by the biomaterial in biomaterial reactor chamber 161 of biomaterial plate 120. The medium flows out through medium outlet channels 1105 to medium outlet manifold 180 in medium delivery plate 125, biomaterial plate 120, and gas delivery plate 115. The medium exits bioreactor 100 through medium outlet 155 in manifold plate 110.

Alternatively, $CO_2$ may be supplied with the $H_2$ gas; or $CO_2$ may be supplied with both the $H_2$ gas and the medium. Alternatively, in one embodiment, a different gas may be introduced from each side (such as $H_2/O_2$) of the biomaterial reactor chamber, and the medium may be flowed slowly through the biomaterial reactor chamber to provide mixing within the biomaterial reactor chamber. In such an embodiment, of course, the innermost membranes about the biomaterial may be hydrophobic.

In one embodiment, membrane 195 in biomaterial plate 120 mitigates or governs the concentrations of reactants in the interaction between the $H_2$ gas in gas reactor chamber 160 in gas delivery plate 115 and the $CO_2$ and the $O_2$ in the medium in medium reactor chamber 162 in medium delivery plate 125. In one embodiment, the biomaterial on membrane 195 may consume the $H_2$ from gas reactor chamber 160 in gas delivery plate 115 and the $CO_2$ and $O_2$ in the medium in medium reactor chamber 162 in medium delivery plate 125 and metabolizes them to the bio-based product. In one embodiment, the bio-based product may flow out with the medium and can be separated in a distillation process.

The process is easily scalable by adding plates to the reactor. For example, instead of end plate 130 after medium delivery plate 125, there may be another biomaterial plate 120, and gas delivery plate 115. The addition may be extended to tens or hundreds of plates.

If there is a puncture in membrane 195 and $O_2$ leaks into the $H_2$, there is only a small volume of $H_2$ present in gas reactor chamber 160 in gas delivery plate 115, so any energy discharge if the $O_2$ and $H_2$ ignite would be small. Flame arrestors may also be included to quench any flame front generated to further reduce the danger of explosion. The flame arrestors may be located in one or more of the gas manifolds, the gas reactor chamber, the medium manifolds, or the medium reactor chamber. Suitable flame arrestors include, but are not limited to, wire mesh, or metal, plastic, or ceramic foam materials.

The invention claimed is:

1. A method for making a bio-based product, the method comprising:
   introducing $H_2$ gas into a gas reactor chamber of a bioreactor in fluid communication with a first side of a biomaterial reactor chamber containing biomaterial to form a gas phase;

introducing medium containing $O_2$ into the bioreactor on a second opposite side of the biomaterial reactor chamber to form a medium phase, the biomaterial reactor chamber comprising a membrane that provides a seal between the gas phase and medium phase;

introducing $CO_2$ into the bioreactor on the first side, the second side, or both, wherein the biomaterial produces the bio-based product from the $H_2$, the $CO_2$, and the $O_2$;

outletting the bio-based product from the bioreactor; and removing the $H_2$ gas from the gas reactor chamber through a gas outlet manifold and a gas outlet, wherein gas and medium reactor chambers are on each side of bioreactor chamber so that gas may be supplied on one side of the biomaterial reactor through a gas inlet, the gas passing across biomaterial and exiting the bioreactor at an opposite end through a gas outlet, and medium may be supplied to the bioreactor from a side adjacent to the gas inlet, the medium supplied through a medium inlet passing across the biomaterial and exiting the bioreactor at an opposite end through a medium outlet.

2. The method of claim 1, wherein the bio-based product is outletted from the bioreactor with the medium, with the $H_2$ gas, or with both.

3. The method of claim 1, wherein one or more of: introducing $H_2$ gas into the bioreactor comprises introducing the $H_2$ gas through a gas inlet to a gas inlet manifold to a gas reactor chamber on the first side of the biomaterial reactor chamber; and introducing the medium into the bioreactor comprises introducing the medium through a medium inlet to a medium inlet manifold to a medium reactor chamber on the second side of the biomaterial reactor chamber.

4. The method of claim 3, further comprising one or more of: removing the medium from the medium reactor chamber through a medium outlet manifold and a medium outlet; and wherein the bio-based product is outletted from the bioreactor with the medium, separating the bio-based product from the medium by distillation.

5. A method for making a bio-based product, the method comprising:

introducing $H_2$ gas into a gas reactor chamber of a bioreactor in fluid communication with a first side of a biomaterial reactor chamber containing biomaterial;

introducing medium containing $O_2$ into the bioreactor on a second opposite side of the biomaterial reactor chamber;

introducing $CO_2$ into the bioreactor on the first side, the second side, or both, wherein the biomaterial produces the bio-based product from the $H_2$, the $CO_2$, and the $O_2$;

outletting the bio-based product from the bioreactor; and removing the $H_2$ gas from the gas reactor chamber through a gas outlet manifold and a gas outlet, wherein the bioreactor comprises: a manifold plate having a gas inlet, a gas outlet, a medium inlet, and a medium outlet; a gas delivery plate having a gas reactor chamber, a gas inlet manifold in fluid communication with the gas reactor chamber, a gas outlet manifold in fluid communication with the gas reactor chamber, a medium inlet manifold in fluid communication with the medium inlet, and a medium outlet manifold in fluid communication with the medium outlet; a biomaterial plate having the biomaterial reactor chamber, a gas inlet manifold in fluid communication with the gas delivery plate gas inlet manifold, a gas outlet manifold in fluid communication with the gas delivery plate gas outlet manifold, a medium inlet manifold in fluid communication with the gas delivery plate medium inlet manifold, and a medium outlet manifold in fluid communication with the gas delivery plate medium outlet manifold; a medium delivery plate having a medium reactor chamber, a gas inlet manifold in fluid communication with the biomaterial plate gas inlet manifold, a gas outlet manifold in fluid communication with the biomaterial plate gas outlet, a medium inlet manifold in fluid communication with the medium reactor chamber and the biomaterial plate medium inlet manifold, and a medium outlet manifold in fluid communication with the medium reactor chamber and the biomaterial plate medium outlet manifold; and an end plate.

* * * * *